(12) United States Patent
Dinsmore

(10) Patent No.: US 6,324,923 B1
(45) Date of Patent: *Dec. 4, 2001

(54) DYNAMIC HEADSPACE OUTGASSING SYSTEM

(75) Inventor: Michael Paul Dinsmore, Longmont, CO (US)

(73) Assignee: Seagate Technology LLC, Scotts Valley, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/547,772

(22) Filed: Apr. 12, 2000

Related U.S. Application Data

(62) Division of application No. 09/315,310, filed on May 20, 1999, now Pat. No. 6,119,534.
(60) Provisional application No. 60/116,566, filed on Jan. 21, 1999.

(51) Int. Cl.[7] ....................................................... G01N 7/14
(52) U.S. Cl. ........................................................... 73/863.12
(58) Field of Search ........................... 73/863.25, 863.11, 73/863.12, 863.21, 864.81, 864.91, 38; 220/565, 581, 582, 495.1, 495.04, 327, 328, 86.1, 917

(56) References Cited

U.S. PATENT DOCUMENTS

| | | |
|---|---|---|
| 4,060,394 * | 11/1977 | Grebe et al. . |
| 4,805,443 * | 2/1989 | Schroeder . |
| 5,237,878 * | 8/1993 | Hackenberg . |
| 5,363,707 | 11/1994 | Augenblick et al. . |
| 5,646,334 | 7/1997 | Scheppers et al. . |
| 5,708,219 | 1/1998 | Scheppers et al. . |
| 5,728,927 * | 3/1998 | Ong . |
| 5,753,791 | 5/1998 | Scheppers et al. . |
| 5,773,707 | 6/1998 | Scheppers et al. . |
| 5,792,423 | 8/1998 | Markelov . |
| 5,800,692 * | 12/1998 | Naylor et al. . |
| 5,849,597 * | 12/1998 | Tokuoka et al. . |
| 5,859,356 | 1/1999 | Scheppers et al. . |
| 5,869,741 | 2/1999 | Scheppers et al. . |

* cited by examiner

Primary Examiner—Robert Raevis
(74) Attorney, Agent, or Firm—John B. Phillips; Merchant & Gould P.C.

(57) ABSTRACT

A method and apparatus for collecting outgassed compounds during a dynamic headspace outgassing test includes placing a component to be tested within a sample container formed from an inert material and placing the container within an oven to heat the component. A gas inflow line directs a flow of inert gas to envelop the component within the sample container and mix with the compounds outgassed from the component. An outflow line formed from an inert material directs the mixture of inert gas and outgassed compounds from the sample container to a trap which separates the inert gas from the outgassed compounds and retains the outgassed compounds for further analysis. The sample container includes a body and a top formed from an inert material and fasteners securing the body and top together to seal the component within an interior chamber of the container.

18 Claims, 6 Drawing Sheets

DYNAMIC HEADSPACE OUTGASSING SYSTEM

RELATED APPLICATION

This application is a division of U.S. application Ser. No. 09/315,310, filed May 20, 1999 now U.S. Pat. No. 6,119,534 which claims benefit of U.S. Provisional Application No. 60/116,566, entitled DYNAMIC HEADSPACE OUTGASSING SYSTEM, filed Jan. 21, 1999.

FIELD OF THE INVENTION

The present invention relates to collecting chemicals and chemical compounds outgassed by a sample in a testing container. More particularly, the present invention relates to a system for collecting outgassed compounds by first heating the sample within an inert testing container and then passing a flow of an inert gas through the inert testing container to collect the outgassed compounds for further analysis.

BACKGROUND OF THE INVENTION

It is well known that complex electromechanical devices, such as computer disc drives, can be harmed by foreign substances which come into contact with vital components of the device. For example, dirt or dust particles which accumulate on the platters of a disc drive can damage the read/write head of the drive causing a "crash." Thus, such devices are typically manufactured within a clean room environment and are sealed prior to leaving the clean room to reduce or prevent the possibility of such contamination.

However, the current breed of disc drives spin much faster and are more densely packed with data than prior drives. These speed and size increases require that the read/write heads fly very close to the surface of the disc platters (on the order of a micron). In light of these very low fly heights, it is possible for matter smaller than common dust or smoke particles to cause head/disc crashes. Indeed, even chemicals or chemical compounds which are outgassed by the disc drive may be sufficiently large to interfere with the drive heads.

Although some disc drive components outgas chemicals and chemical compounds while the drive is inactive, the level of outgassing typically increases when the drive is operating and the components are exposed to high temperatures. These outgassed chemicals and chemical compounds are easily transported throughout the drive (due to the rotation of the disc platters and the resulting air currents within the sealed drive) where they typically bond to the substrate that coats the disc platters. In addition to physically interfering with the drive heads during operation of the drive, some outgassed compounds (e.g., adhesives) may react chemically with the drive heads during periods of inactivity when the heads are in direct contact with the disc platters. Such chemical reactions cause stiction between the heads and the disc platters which further contributes to early disc drive failure.

Thus, it is important for disc drive manufacturers (as well as manufacturers of other electromechanical devices which may be susceptible to damage from outgassed compounds) to carefully inspect all of the components which make up the drive for the presence of outgassed compounds. Examples of such components within a disc drive include motors, coil bobbins, magnets, adhesives and labels.

Inspections of such individual components are typically conducted by static headspace sampling where a component (such as a drive head) is placed within a small, sealed container and held at an elevated temperature until the outgassed compounds reach a state of equilibrium within the headspace. The term "headspace" is utilized herein to refer to the space within the sealed container which is not taken up by the tested component itself. The sealed container typically includes an open top sealed by a septum to allow a needle to penetrate the headspace and withdraw a sample of the equilibrated headspace. This sample is then analyzed using known techniques and equipment such as a gas chromatograph and a mass spectrometer to determine the composition of the different outgassed compounds.

However, this prior "static" approach suffers from a number of problems, foremost of which is that only a small amount of the headspace volume (approximately 1 milliliter) may be withdrawn by the syringe before the equilibrium within the sealed container is upset. This small sample reduces the sensitivity (i.e., increases the detection threshold) of the test so that the levels of the outgassed compounds may not be accurately measured, while other outgassed compounds may not be detected at all. A further drawback to the prior art static testing is that the sealed containers are typically of limited size so that larger components (such as disc drive spindle motors or coil bobbins) can not fit within the containers. These relatively large components are typically sectioned so that only a portion of the larger component is placed within the container. However, the cutting process, and the heat generated thereby, may contaminate the results of the headspace outgassing test. Furthermore, analyzing relatively small, exposed sections of larger components may artificially shield or increase important outgassing constituents.

The above problems associated with traditional "static" headspace outgassing tests have increased the interest in "dynamic" testing procedures. Simply put, a "dynamic" test utilizes a flow of gas within a testing container (i.e., within the "headspace" of the container) over a period of time to collect the outgassed compounds. This "carrier gas" is preferably an inert or neutral gas which does not react with any of the outgassed compounds. The inert gas thus carries the outgassed compounds from the headspace to the analytical equipment which analyzes the compounds. One example of a "dynamic" headspace sampling system is described in U.S. Pat. No. 5,646,334 entitled MULTI-SAMPLE DYNAMIC HEADSPACE SAMPLER, issued Jul. 8, 1997 to Scheppers et al., and assigned to the assignee of the present invention.

However, several aspects of the prior dynamic testing systems can be improved upon, including the accuracy and sensitivity of the test as well as the length of time required for the testing procedure. Specifically, prior dynamic testing containers typically comprise disposable jars such as glass masonjars having a threaded top. While the disposable glassjar is inexpensive, glass is not an inert material and thus the jar itself will contribute outgassed compounds over the course of the test, particularly as the jar is held at an elevated temperature for a number of hours. Next, an aluminum top having both an inlet and an outlet for the carrier gas is typically screwed to the top of the jar to define a sealed testing chamber. The upper location of both the inlet and the outlet reduces the "flushing efficiency" of the testing chamber since outgassed compounds at the bottom of the jar are not flushed from the testing chamber at the same rate as compounds at the top of the jar. Additionally, relatively heavy compounds at the bottom of the jar may not be captured at all due to the tendency of the carrier gas to remain in the upper portion of the jar. Furthermore, like the glass jar itself, the aluminum top is not inert and will also contribute to anomalous results. To account for the extra contributions from both the glass jar and the aluminum top, a "blank" must typically be included with each test run to determine the types and amounts of compounds outgassed by the container itself. The time required to test a blank container with each test run, together with the possible errors introduced with the analysis of each "blank," represents a large degree of inefficiency and uncertainty with the prior dynamic testing systems.

In addition to contributing their own outgassed compounds, the non-inert glass jar and aluminum top may also bond with those compounds which are outgassed by the sample, thereby reducing the sensitivity of the test. Furthermore, although the prior art containers typically include seals positioned between the jar and the top, the glass jar and the aluminum top have different expansion coefficients and thus tend to expand at different rates as they are heated. Such differing rates of expansion increase the likelihood of leaks which further contaminate the test results.

A further problem relating to "dynamic" testing systems is the requirement that the sample be maintained at an elevated temperature while still providing for gas lines running to and from the testing container. Previous dynamic testing systems address this problem by placing the containers upon a heated block during the duration of the test. However, while the heated block provides unimpeded access to the top portion of the container for connection of gas inlet and outlet lines, the block only applies heat to the bottom of the testing container which produces an undesirable temperature gradient within the sealed testing chamber (i.e., warmer at the bottom than at the top). The problem of uneven heating is further complicated by the position of both the inlet and the outlet for the inert carrier gas at the top of the container. Since the carrier gas itself is not heated, the inflow of the relatively cool gas at the top of the chamber further increases the temperature gradient between the top and bottom of the chamber. Uneven heating of the chamber makes it difficult to achieve equilibrium within the headspace and thus tends to dramatically increase the time required to collect a sample of the outgassed compounds, sometimes requiring up to 24 hours. Furthermore, the temperature gradient and the flow of a relatively cool gas at the top of the chamber tends to cause some of the outgassed compounds within the chamber to condense on the aluminum top, thereby further reducing the sensitivity of the test.

It is with respect to these and other background considerations, limitations and problems that the present invention has evolved.

SUMMARY OF THE INVENTION

The present invention provides an apparatus and a method for dynamically sampling outgassed chemicals and chemical compounds within the headspace of a sample container.

In accordance with a preferred embodiment of the present invention, a sample container is provided for holding components to be tested during a dynamic headspace outgassing test. The sample container includes a preferably cylindrical body and a top which are combined to form an interior chamber for holding the component during the dynamic test. The body and top are both formed from an inert material to prevent contamination of the headspace by outgassed compounds from the body or top, and to further prevent any interaction between the body or top and any compounds outgassed by the component. Inflow and outflow connectors attached to openings within the body and the top allow a flow of a heated, inert gas to pass through the headspace of the chamber and remove outgassed compounds for analysis.

A preferred embodiment of the present invention also includes apparatus for collecting outgassed compounds during a dynamic headspace outgassing test. The apparatus includes a container formed from an inert material, an oven for heating the container, and a flow controller for providing a flow of inert gas to an interior chamber of the container which receives the component to be tested. An inflow line connected to the container directs the flow of inert gas through the headspace of the chamber to mix with the outgassed compounds. An outflow line formed from an inert material then directs the mixture of inert gas and outgassed compounds to a trap which separates the outgassed compounds from the inert gas for later analysis.

The preferred embodiment of the present invention further includes a method of collecting outgassed compounds from a component over the course of a predetermined test period. The method includes placing the component within a container formed from an inert material and then placing the container within an oven to heat the component within the container. An inert gas is first heated as it passes through the oven and is then supplied to an interior chamber within the container to mix with the chemicals and compounds outgassed from the component. The mixture of inert gas and outgassed compounds is then directed to a trap where the outgassed compounds are separated from the inert gas and retained within the trap.

A more complete appreciation of the present invention and its scope may be obtained from the accompanying drawings, which are briefly summarized below, from the following detailed description of presently preferred embodiments of the invention, and from the appended claims.

These and various other features as well as advantages which characterize the present invention will be apparent from a reading of the following detailed description and a review of the associated drawings.

DETAILED DESCRIPTION OF THE PREFERRED EMBODIMENTS

Figure 1:
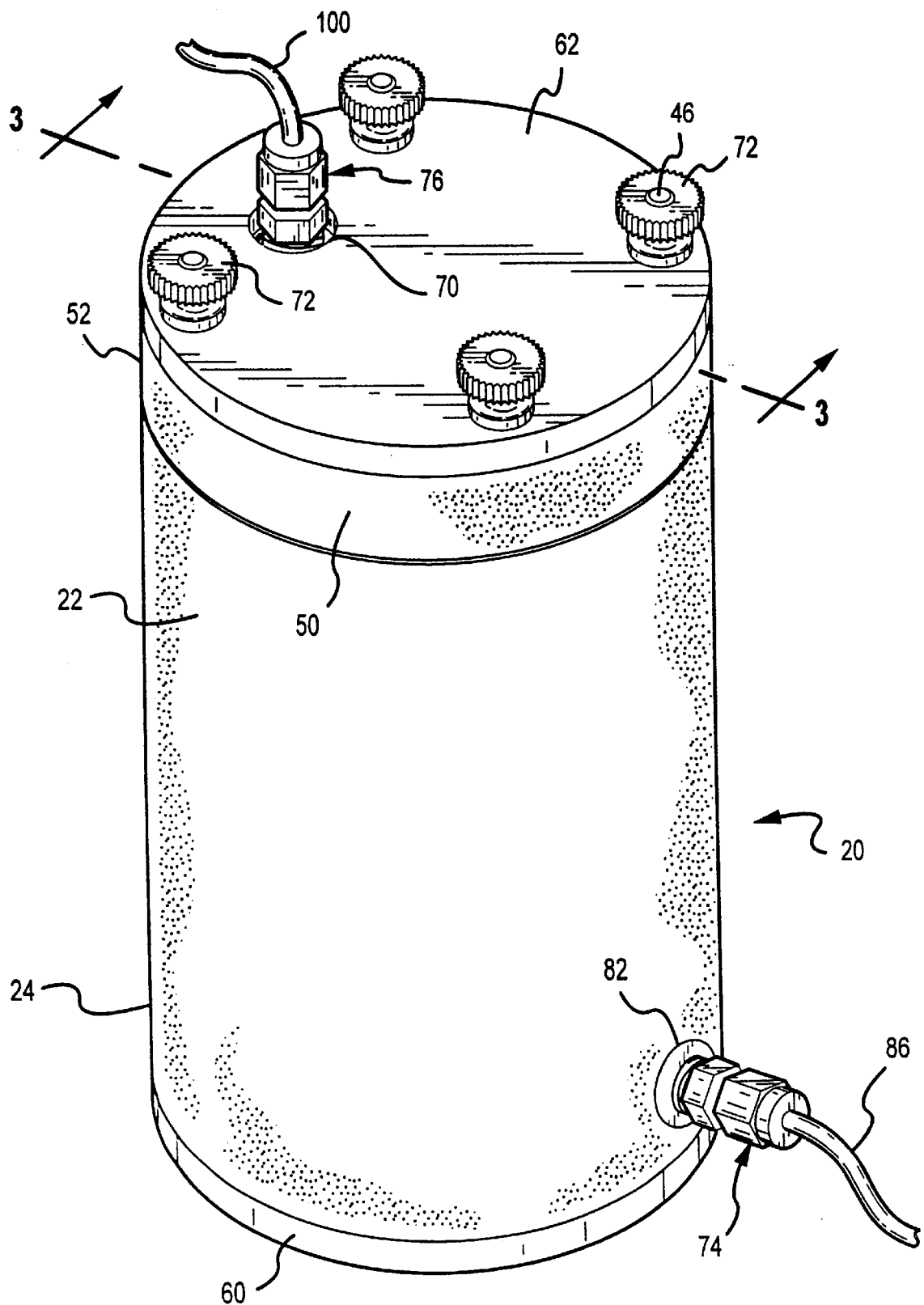
FIG. 1 is an isometric view of a test container used within the dynamic headspace outgassing system in accordance with a preferred embodiment of the present invention.
Figure 2:
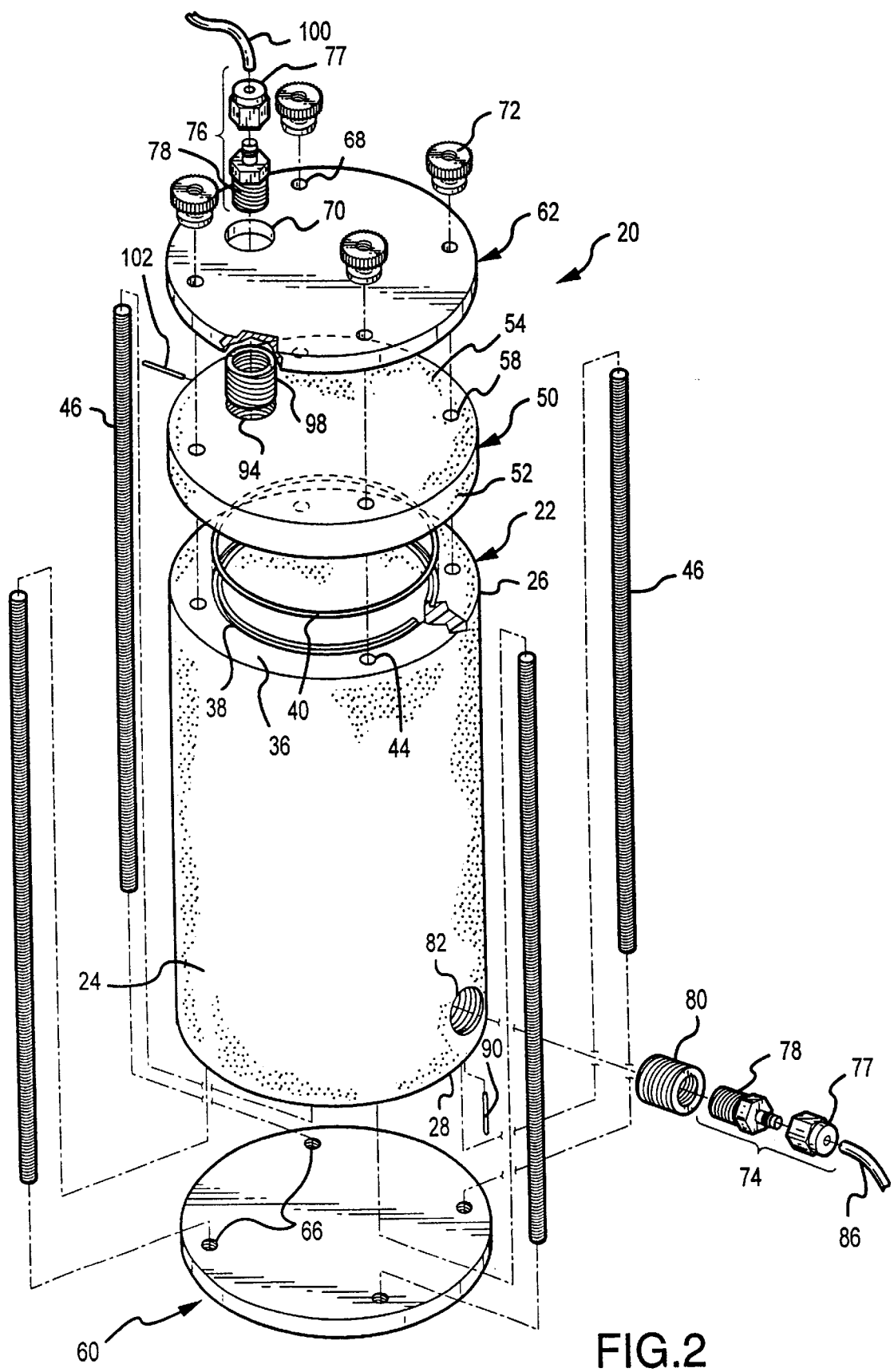
FIG. 2 is an exploded view of the test container shown in FIG. 1.
Figure 3:
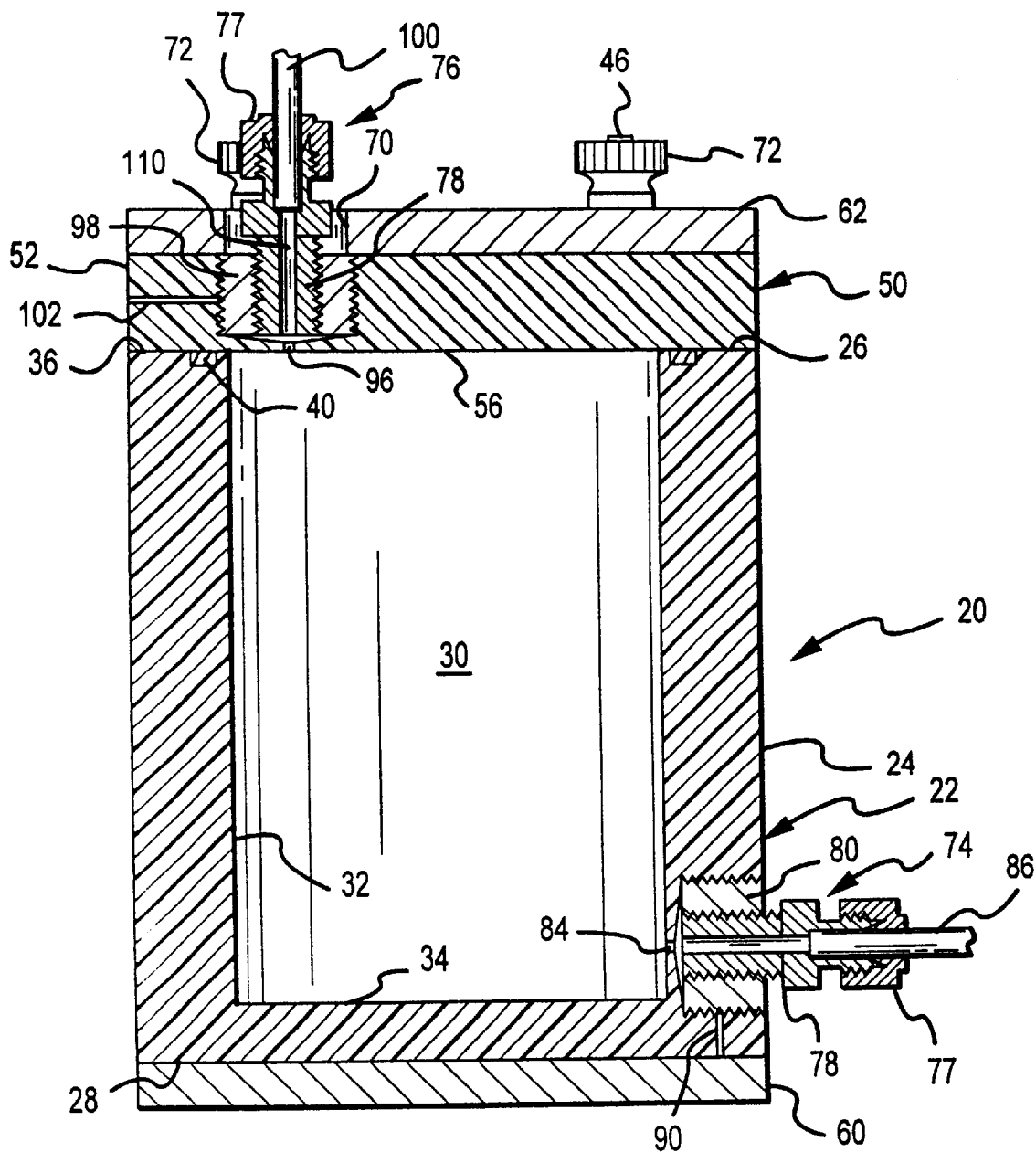
FIG. 3 is a section view taken substantially along the line 3—3 in FIG. 1.

FIGS. 1–3 illustrate a preferred embodiment of a sample container 20 of the present invention. The sample container 20 includes a substantially cylindrical body 22 formed from an inert material such as Teflon. The cylindrical body 22 includes an outer surface 24, a top end 26 and a bottom end 28. A bore formed from the top end 26 (FIG. 3) defines an interior chamber 30 for holding sample components to be tested. The interior chamber 30 is open at the top end 26 and is bounded by a cylindrical interior wall 32 and a bottom surface 34.

An annular rim 36 surrounding the open top end 26 of the chamber 30 includes an annular groove 38 formed therein for receiving a rubber O-ring 40, described in greater detail below. A plurality of through holes 44 (FIG. 3) are preferably formed lengthwise between the top and bottom ends 26 and 28 of the body 22. The holes 44 are spaced equidistantly around the rim 36 and are preferably positioned radially between the 0-ring 40 and the outer surface 24. Each through hole 44 allows for passage of a threaded rod 46 through the body 22, as described in greater detail below.

The sample container 20 further includes a chamber top 50 which is also preferably formed from Teflon or another inert material. Indeed the chamber top 50 preferably comprises a cylindrical section having a diameter equal to an outer diameter of the cylindrical body 22. The cylindrical chamber top 50 includes an outer surface 52, a top surface 54, and a bottom surface 56. The bottom surface 56 is adapted to contact the 0-ring 40 of the body 22 to hermetically seal the interior chamber 30 as described in greater detail below. Additionally, a plurality of through holes 58 (FIG. 3) are preferably formed between the top and bottom surfaces 54 and 56, respectively, of the chamber top 50. The through holes 58 are spaced to line up with the through holes 44 when the chamber top 50 is placed atop the body 22.

To ensure a tight seal between the body 22 and the chamber top 50, a pair of stainless steel plates 60 and 62 cooperate with the threaded rods 46 to compress the body 22 and the chamber top 50 together. Specifically, the bottom cylindrical plate 60, having the same diameter as that of the chamber top 50 and the outer diameter of the body 22, includes a plurality of threaded holes 66 (FIG. 3) positioned for alignment with the holes 44 in the body 22. The top cylindrical plate 62 includes a plurality of through holes 68 aligned with the through holes 58 in the chamber top 50. The top cylindrical plate 62 also includes a through hole 70 described in greater detail below.

Once the threaded rods 46 have been secured within the threaded holes 66 in the bottom plate 60, the cylindrical body 22, the chamber top 50 and the stainless steel top plate 62 may be stacked upon the bottom plate 60 as shown in FIG. 2 by passing the threaded rods 46 through the through holes 44, 58 and 68, respectively. Thumb nuts 72 are then preferably secured to a top end of each of the rods 46 protruding above the top plate 62 and tightened against the top plate 62 (FIGS. 1 and 3) to compress the chamber top 50 against the rim 36 and the O-ring 40 of the body 22. Compressed in this manner, the chamber top 50 and the body 22 form a hermetic seal around the interior chamber 30 of the body 22. Thus, a test sample (e.g., a component of a disc drive) may be easily loaded and unloaded from within the container 20 by simply unscrewing the thumb nuts 72 and lifting the top plate 62 and the chamber top 50 off of the rim 36 of the body 22. Although four threaded rods 46 are described in the preferred embodiment, it is understood that a larger or smaller number of rods 46 may be used as long as an airtight seal is achieved between the body 22 and the top 50.

Once a test sample has been placed within the interior chamber 30 of the body 22, the "dynamic" testing process of the present invention requires that an inert gas must flow through the "headspace" around the test sample and then out of the body 22 to carry away any chemicals or compounds which have been outgassed by the test sample. The gas preferably flows in at the bottom of the headspace and flows out from the top of the headspace to completely envelop the test sample. Toward this end, gas inflow and outflow connectors 74 and 76 are connected to the bottom of the of the body 22 and the chamber top 50, respectively. The connectors 74 and 76 are preferably of the type manufactured by Swagelok™ which include a connector portion 77 for receiving an end of a gas line and a threaded portion 78 for securing the connector to a gas port, and are well known to those skilled in the art.

The threaded portion 78 of the gas inflow connector 74 is secured within an interior threaded opening of a bushing 80. The bushing 80 ferer includes external threads for securing the bushing 80 within a threaded opening 82 formed in the outer surface 24 of the Teflon body 22. The threaded opening 82 does not penetrate the interior wall 32 of the body 22, but rather communicates with a through hole 84 (FIG. 3) having a much smaller diameter (approximately 0.10 inches) which in turn communicates with the interior chamber 30 of the body 22. In this manner, a gas inflow tubing 86 inserted within the Swagelok™ inflow connector 74 is placed in fluid communication with the interior chamber 30 of the body 22 once the threaded portion 78 of the connector 74 is screwed into the bushing 80 in the side of the body 22. Additionally, due to the soft nature of the Teflon body 22, a locking pin 90 is preferably utilized to prevent the threaded bushing 80 from working itself out of the threaded opening 82. The locking pin 90 (FIGS. 2 and 3) is inserted through the bottom end 28 of the body 22 so that an end of the pin 90 extends between adjacent threads of the bushing 80 to prevent the bushing from spinning within the threaded opening 82.

The gas outflow connector 76 is attached to the chamber top 50 in a manner similar to the connection of the gas inflow connector 74 described above. Specifically, a threaded opening 94 formed in the top surface 54 of the chamber top 50 communicates with a smaller-diameter through hole 96 to provide access to the interior chamber 30 of the body 22. A bushing 98 is secured within the threaded opening 94 and the threaded portion 78 of the gas outflow connector 76 is secured to an interior threaded opening of the bushing 98. A gas outflow tubing 100 made of inert material such as Teflon may then be inserted within the connector 76 to allow the inert carrier gas and any outgassed compounds to exit the interior chamber 30 of the body 22. A locking pin 102 (FIGS. 2 and 3) is preferably inserted through the outer surface 52 of the chamber top 50 to prevent the bushing 98 from spinning within the soft Teflon material of the threaded opening 94 in the chamber top 50. Furthermore, the through hole 70 in the top steel plate 62 is preferably aligned with the outflow connector 76 to prevent interference between the connector 76 and the plate 62 during assembly of the container 20 and to allow the connector 76 to extend above the plate 62 for connection with the tubing 100.

Figure 4:
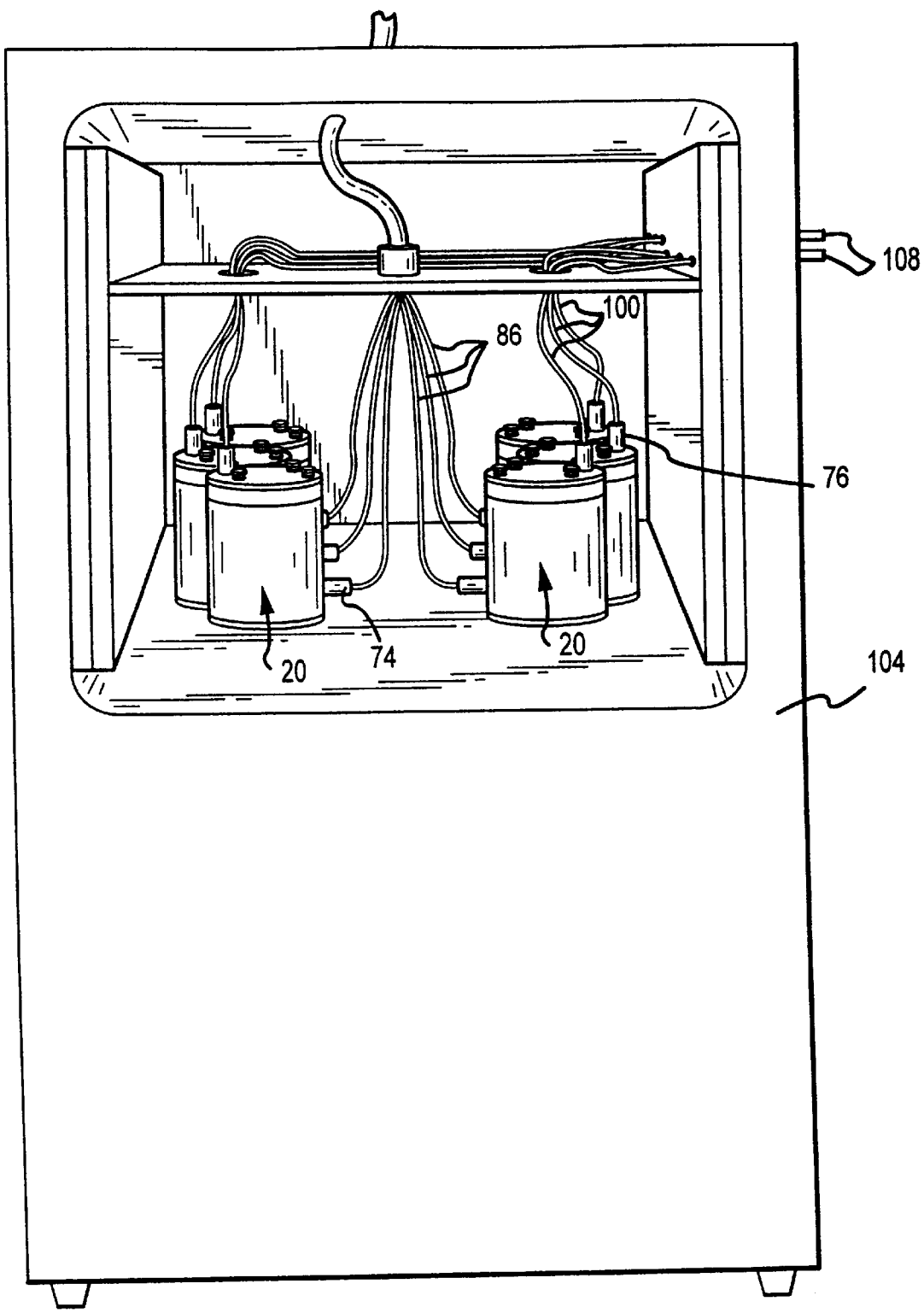
FIG. 4 is an isometric view of an oven containing a plurality of the test containers shown in FIG. 1 together with a plurality of gas inflow and outflow lines extending outside of the oven.

Once a component to be tested has been placed on the bottom surface 34 of the body 22 and sealed within the interior chamber 30, the entire container 20 is preferably placed inside an oven 104 (FIG. 4). The gas inflow and outflow lines 86 and 100 pass through walls of the oven 104 for connection to the inflow and outflow connectors 74 and 76, respectively. The headspace outgas sampling test is then conducted by heating the sample containers 20 to a temperature of approximately 85° C. for a period of time preferably ranging between one and three hours. During the course of the test, an inert, heated carrier gas such as nitrogen flows through the headspace of the interior chamber 30 and carries the outgassed compounds out of the oven 104 through the outflow line 100 to a trap 108 on the exterior of the oven 104. The trap 108 preferably comprises a cylindrical tube which is packed with activated carbon or other similar absorbents that bonds with the outgassed compounds while allowing the inert nitrogen gas to pass harmlessly to the atmosphere. At the conclusion of the test, the contents of the carbon trap 108 are desorbed and analyzed with standard equipment such as a gas chromatograph and a mass spectrometer to determine the composition of the outgassed chemicals and compounds. In a preferred embodiment, the collection phase of the test is conducted over a three-hour period to allow for two complete test cycles and analyses over the course of typical workday. The specific testing procedure and apparatus for conducting multiple outgas sampling tests at one time are described in greater detail below.

As described above, the body 22 and the chamber top 50 are preferably formed from Teflon to reduce or eliminate any contribution to the outgassed compounds due to the sample container 20 itself. While other substantially inert materials such as Delrin or polypropylene may be substituted for Teflon, Teflon is preferred because it is essentially inert at the preferred testing temperature (e.g., 85° Celsius) and thus represents an improvement over prior art glass or steel containers which may contribute their own outgassed compounds at those temperatures. Additionally, non-inert materials such as glass or stainless steel tend to bond with some of the outgassed compounds from the test sample such as acids or other sulfur compounds. These prior art sample containers can thus produce inaccurate results since the outgassed compounds that bond to the surfaces of the sample containers will be absent from the sample sent to the analysis equipment.

The present sample container 20 provides that the outgassed compounds within the headspace, together with the carrier gas, will only contact Teflon surfaces within the sample container. Specifically, there are no stainless steel parts exposed within the interior chamber 30 of the body 22. To further reduce the possibility of contamination, the outflow line 100 is also preferably made from Teflon so that the heated, outgassed compounds will not bond with the outflow line, thereby ensuring that substantially all of the outgassed compounds are passed to the trap 108. Furthermore, the Teflon outflow line 100 is preferably inserted as far as possible within the connector portion 77 of the Swagelok™ outflow connector 76 to again minimize the exposure of the outgassed compounds to the stainless steel material of the connector 76. Specifically, the end of the Teflon outflow line 100 abuts the threaded portion 78 of the Swagelok™ outflow connector 76 that mates with the bushing 98 so that the outflow gas is only exposed to stainless steel along a very short (approximately 1 cm.) passage 110 within the connector 76. This small exposure is not believed to contribute any measurable degree of error to the analysis of the outgassed compounds.

In one embodiment, the inflow line 86 leading from the source of the inert gas to the bottom of the sample container 20 may also be formed of Teflon. However, since the carrier gas passing through the inflow line 86 is an inert gas (preferably grade 5 nitrogen having a purity of 99.99%), a Teflon line is not required. Thus, an alternative embodiment of the inflow line 86 may be formed from stainless steel or other alternative materials since the inflow line 86 will not be exposed to the heated compounds outgassed from the tested component.

Thus, the use of an inert carrier gas and an inert material (preferably Teflon) for the body 22 and the chamber top 50 tends to increase the sensitivity and the accuracy of the test results in comparison to prior art dynamic headspace outgassing systems. While other inert gases (e.g., helium or argon) may be used as the carrier gas, nitrogen is preferred over these other gases on the basis of cost and availability. Similarly, while other inert materials may be used in place of Teflon to form the testing body 22 and top 50 of the container 20, Teflon is preferred due to its soft construction and the ease of manufacturing the body 22 and the top 50.

Due to the tendency of Teflon to change its shape when heated, the stainless steel plates 60 and 62 are preferably used with the threaded rods 46 and the thumb nuts 72 to compress the chamber top 50 against the upper rim 36 of the body 22 and the O-ring 40. The O-ring 40 is preferably formed from an inert rubber such as Viton to prevent contamination of the sample in the event that the O-ring should be exposed to the headspace within the body 22. The steel plates 60 and 62 help to secure the threaded rods 46 within the relatively soft Teflon body 22 and to provide a bearing surface for the thumb nuts 72. In the absence of the plates 60 and 62, the threaded rods 46 would likely work themselves loose from the body 22 and the thumb nuts 72 would likely damage the chamber top 50 after repeated use. While the plates 60 and 62 and the rods 46 are preferably used to secure the container 20, other types of fasteners may be used by those skilled in the art to seal the body 22 to the top 50 without damaging the Teflon material.

While no specific size or shape of the container 20 is required, the interior chamber 30 of the preferred container 20 is approximately 200 milliliters in size, although larger containers 20 may be utilized if needed to accommodate the largest components of a disc drive or other similar electromechanical device. Furthermore, the provision of the inflow connector 74 at the bottom of the container 20 and the outflow connector 76 at the top ensures a thorough mixing of the carrier gas within the headspace so that substantially all of the compounds outgassed by the component will be removed to the trap 108. This bottom-to-top mixing allows a relatively low flow rate of the carrier gas to be used in relation to prior art systems which position both the inflow and outflow connectors at the top of the container. Specifically, a nitrogen gas flow rate of 50 milliliters/minute is preferred, although flow rates within the range of 40–60 milliliters/minute are also acceptable. Such a flow rate operates to exchange the entire 200 milliliter headspace approximately every 4 minutes or approximately 45 times over the course of a three hour test. Therefore, even if the size of the container 20 were increased to provide for a chamber volume of 500 milliliters, the preferred flow rate of 50 milliliters/minute would still exchange the headspace approximately 18 times over the course of a three hour test. Such an exchange rate is sufficient to provide accurate results for the outgassing test.

Thus, the container 20 represents a vast improvement over prior art testing containers which typically comprised disposable glass tubes or jars. The improvement is realized in reduced testing times (e.g., three hours or less) and improved sensitivity and reproducibility of test results. For example, while prior art headspace outgas sampling systems typically detect outgassed compounds with and accuracy of several parts per million, the present invention increases the sensitivity of the test (i.e., reduces the detection threshold) by 1–2 orders of magnitude, thereby allowing measurements of compounds with an accuracy of several parts per billion or even several parts per trillion with sufficiently accurate analysis equipment.

Figure 5:
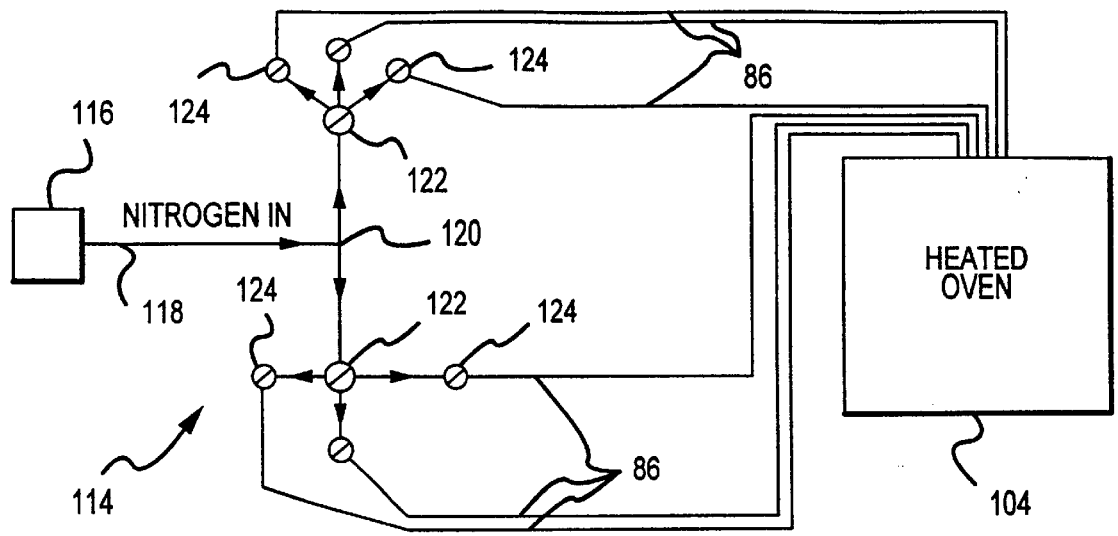
FIG. 5 is a schematic view of a flow controller which directs a flow of an inert gas to each of the containers shown in FIG. 4.
Figure 6:
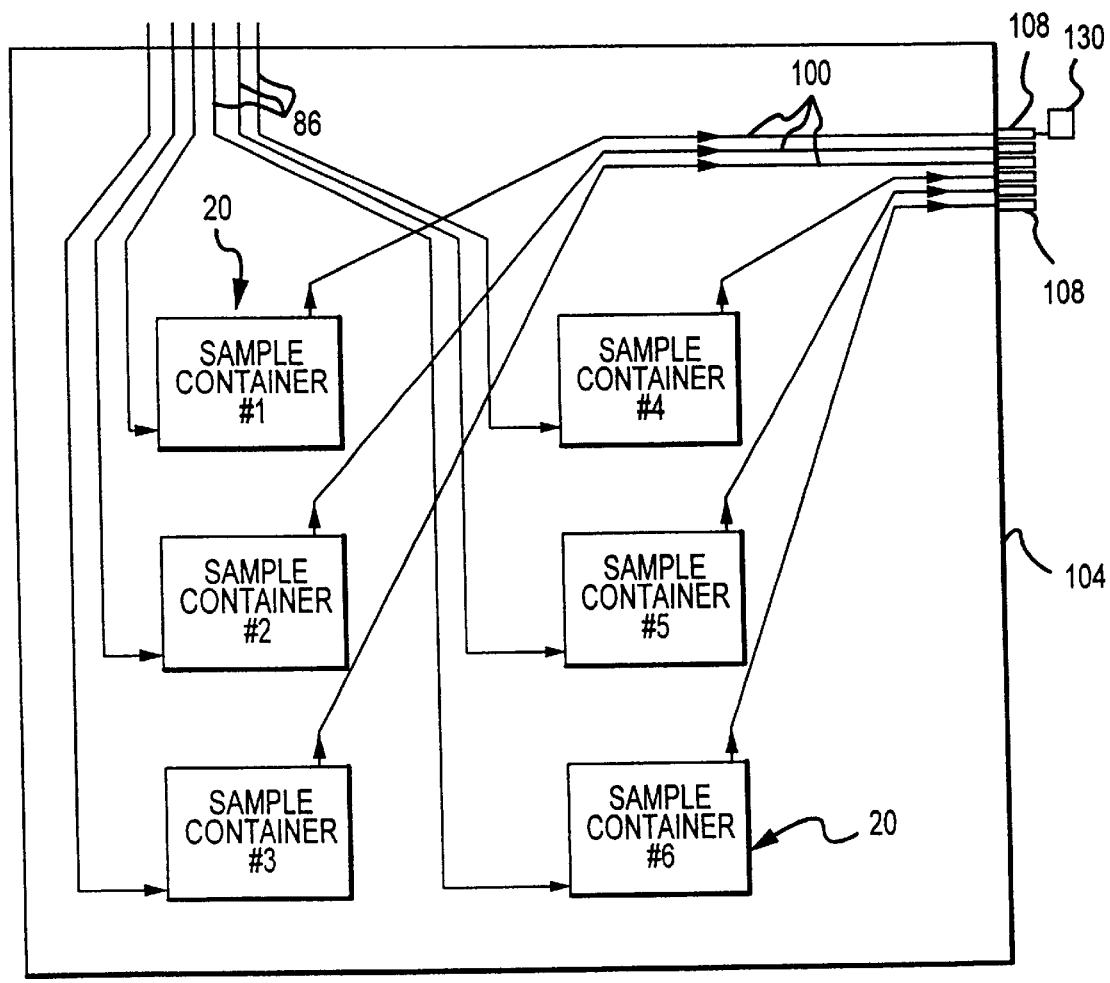
FIG. 6 is a schematic view of the oven and sample containers shown in FIG. 4, further illustrating the outflow lines connecting each of the sample containers to a trap outside of the oven for collecting compounds outgassed during the course of the test.

FIGS. 4–6 illustrate that a plurality of containers 20 are preferably placed within the oven 104 to allow a number of samples to be tested at one time. Preferably six samples are tested simultaneously, although it is understood that larger or smaller numbers of simultaneous tests may be conducted within the scope of the present invention. FIGS. 4 and 6 illustrate that a plurality of inflow lines 86 enter through a sealed opening in the oven 104, with each separate line 86 connected to a inflow connector 74 at the bottom of one of the sample containers 20. As described above, the inflow lines 86 may be alternatively formed from Teflon or stainless steel. Next, a plurality of Teflon outflow lines 100 connect each of the container outflow connectors 76 to one of the traps 108 on the exterior of the oven 104. Placing the traps 108 on the exterior of the oven 104 allows the nitrogen carrier gas to be harmlessly vented to the atmosphere within the testing laboratory during the course of the test.

In order to provide each of the sample containers with the desired flow rate (e.g., 50 milliliters/minute) of the nitrogen carrier gas, a flow control system 114 is utilized as shown schematically in FIG. 5. The flow control system 114 comprises a source 116 of substantially pure nitrogen gas. A line 118 from the source 116 is split at junction 120 to feed two separate mass flow valves 122. Each mass flow valve 122 in turn divides the gas flow between a plurality of individual feeder valves 124. The feeder valves 124 preferably comprise known needle valves, and each valve 124 is connected to one of the containers 20 within the oven 104 by a gas inflow line 86 as described above. In the preferred embodiment, each mass flow valve 122 preferably splits the nitrogen flow into three parts for a total of six feeder valves 124. However, the mass flow valves could divide the flow into more than three parts, or additional mass flow valves 122 could be utilized, if more than six samples were to be tested at one time within the oven 104.

The flow control system 114 is calibrated to supply a specified flow rate to each of the sample containers 20. A flow rate within the range of 40–60 milliliters/minute is preferred, with a flow rate of 50 milliliters/minute being most preferred. Due to the back pressure provided by the carbon traps 108, each of the feeder valves 124 must be adjusted to ensure a proper flow rate through its attached circuit consisting of the inflow line 86, the container 20, the outflow line 100 and the carbon trap 108. The calibration process requires that a flow meter 130 (FIG. 6) be attached to each of the carbon traps 108 while the associated feeder valve 124 for that circuit is adjusted until the flow meter reads the desired flow rate (e.g., 50 milliliters/minute).

Once all six of the feeder valves 124 have been properly adjusted, the flow control system 114 remains calibrated over numerous testing cycles since each of the carbon traps 108 is presumed to provide an identical amount of back pressure or resistance to the circuit. This represents an improvement over prior art flow control systems that require flow calibration prior to each test run. Furthermore, due to the use of the two mass flow valves 122, leaks within the lines may be quickly traced. That is, due to the back pressure provided by the traps 108, any leak within one of the inflow or outflow lines 86 or 100 will cause a short circuit within all three of the gas circuits connected to the respective mass flow valve 122. Thus, a leak will be detected by the lack of any gas outflow from a group of three of the traps 108, and an operator need only check those three gas circuits rather than all six of the circuits as would otherwise be required in the absence of the mass flow valves 122.

Figure 7:
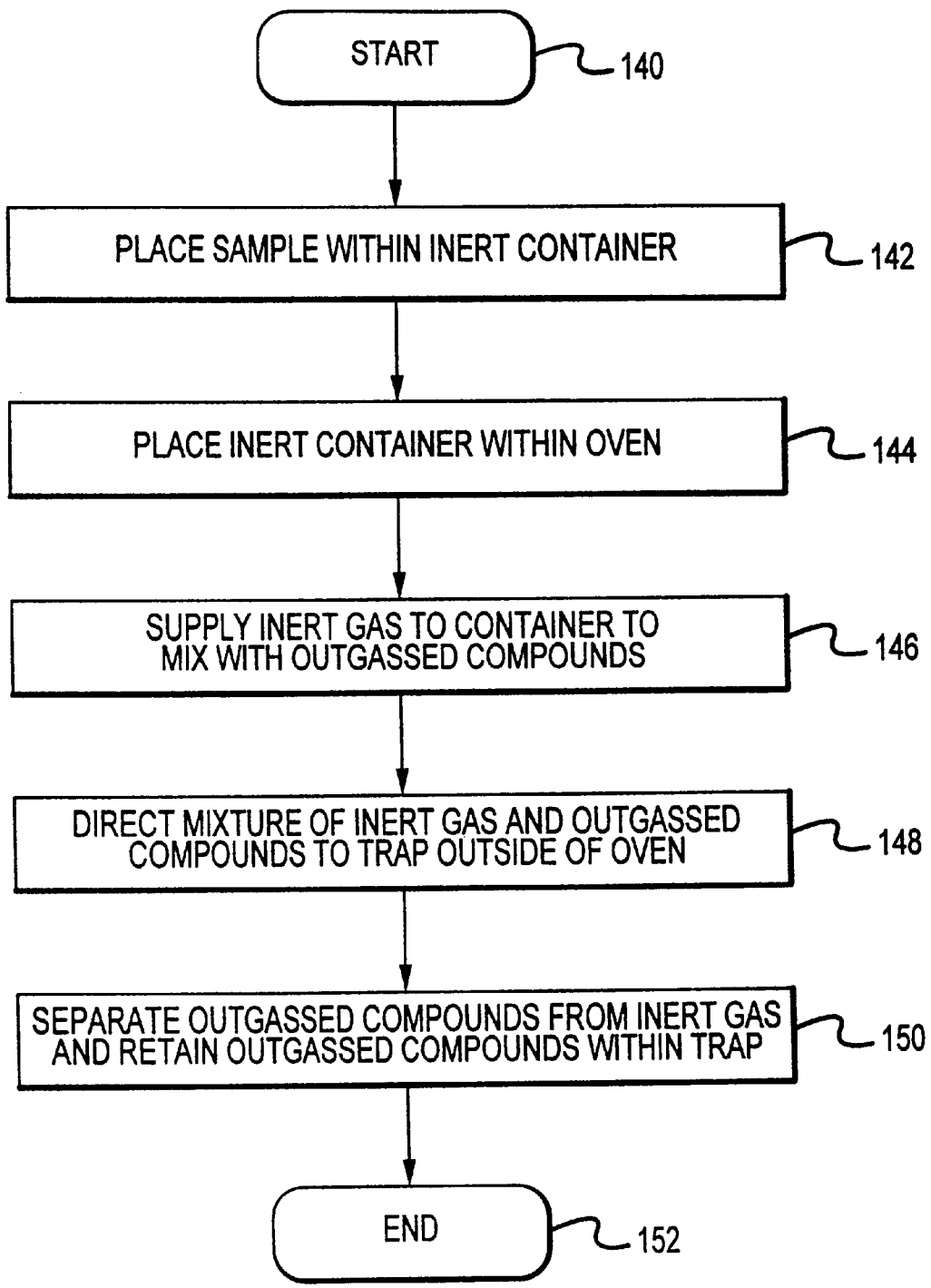
FIG. 7 depicts a flow chart of steps for collecting outgassed compounds in accordance with a preferred embodiment of the present invention.

FIG. 7 depicts a flow chart of steps for collecting outgassed compounds from a component utilizing the inert container 20 shown in FIG. 1. Starting at 140, the first step 142 includes placing the component within a container formed from an inert material. The next step 144 includes placing the container 20 within an oven 104 to heat the component to a predetermined temperature. An inert gas is then supplied to an interior of the container at a predetermined flow rate to mix with the chemicals and compounds outgassed from the component in step 146. The inert gas is preferably heated as it passes through the oven 104 to the container 20. In the next step 148, the mixture of inert gas and outgassed compounds is directed to a trap 108. The final step 150 separates the outgassed compounds from the inert gas and retains those outgassed compounds within the trap 108 before the process stops at 152.

The dynamic headspace outgassing system of the present invention provides a number of benefits and represents a number of improvements over prior art static and dynamic headspace sampling systems. First, the dynamic nature of the test ensures that a true, representative sampling of the outgassed compounds will be collected over the period of the test as opposed to static tests which are only capable of taking a one-time sample of the headspace within the container. The continual collection of outgassed compounds over the course of one or more hours increases the sensitivity of the test results by orders of magnitude over prior art static tests. Additionally, the system of the present invention provides greater accuracy than other known dynamic testing systems due to the use of inert materials (e.g., Teflon) for the collection and transportation of the outgassed compounds to the carbon traps 108. While the Teflon material prevents any of the outgassed compounds from bonding to the sample container 20 or the outflow line 100, the improved design of the sample containers (e.g., the bottom-to-top gas flow) further ensures that all of the outgassed compounds within the headspace will be carried to the carbon trap 108. Furthermore, the use of the oven 104 ensures that the sample containers 20 will be evenly heated, while the placement of both the inflow and outflow lines 86 and 100 within the oven 104 tends to heat the carrier gas so that the carrier gas will not substantially cool the sample over the course of the test. These improvements help to ensure that the sample will achieve and maintain equilibrium over the course of the test, thereby increasing the efficiency of the testing system so that relatively shorter testing times and lower carrier gas flow rates produce more accurate results with a greater degree of sensitivity (i.e., a lower detection threshold) than any prior art testing system.

In summary, the preferred embodiment disclosed herein is directed to an apparatus for dynamically sampling outgassed chemicals and chemical compounds within the headspace of a sample container (such as 20). The sample container (such as 20) includes a body (such as 22) and a top (such as 50) formed from an inert material. Fasteners (such as 46 and 72) secure the body (such as 22) and the top (such as 50) to form an inert interior chamber (such as 30) for holding the component during the dynamic test. An inflow connector (such as 74) is connected to an opening (such as 82) in the container (such as 20) to direct a flow of gas into the chamber (such as 30). An outflow connector (such as 76) is connected to an opening (such as 94) to direct a flow gas out of the chamber (such as 30).

In another preferred embodiment of the present invention, the body (such as 22) and the top (such as 50) of the container (such as 20) are formed from Teflon.

In another preferred embodiment of the present invention, an inert rubber seal (such as 40) attached to the body (such as 22) hermetically seals the chamber (such as 30) when the top (such as 50) is secured to the body.

In another preferred embodiment of the present invention, the fasteners include threaded rods (such as 46) extending from the body (such as 22) and aligned with openings (such as 58) in the top (such as 50). Nuts (such as 72) engage the threaded rods (such as 46) to secure the top (such as 50) to the body (such as 22).

In another preferred embodiment of the present invention, the fasteners include a top steel plate (such as 62) and a bottom steel plate (such as 60) that receive the threaded rods (such as 46) and bear against top and bottom surfaces (such as 54 and 28) of the container (such as 20).

In another preferred embodiment of the present invention, the top steel plate (such as 62) includes an opening (such as 70) to allow the outflow connector (such as 76) to extend above the container (such as 20) for connection to an outflow line (such as 100).

In another preferred embodiment of the present invention, the outflow line (such as 100) is formed from an inert material such as Teflon.

A further preferred embodiment of the present invention includes apparatus for collecting outgassed compounds from a sample. The apparatus includes a container (such as 20) formed from an inert material for holding the sample and an oven (such as 104) for heating the container to a predetermined temperature. A flow controller (such as 114) provides a flow of inert gas to an interior chamber (such as 30) of the container (such as 20) via an inflow line (such as 86). An outflow line (such as 100) then directs the mixture of inert gas and outgassed compounds from the chamber (such as 30) to a trap (such as 108) which separates the outgassed compounds from the inert gas for later analysis.

In another preferred embodiment of the present invention, the container (such as 20) and the outflow line (such as 100) are formed from an inert material such as Teflon.

In another preferred embodiment of the present invention, a flow meter (such as 130) connected to the trap (such as 108) measures a flow rate of the inert gas exhausted from the trap.

In another preferred embodiment of the present invention, a number of containers (such as 20) are positioned in an oven (such as 104) and a number of inflow lines (such as 86) are connected between a flow controller (such as 114) and the containers (such as 20) to direct inert gas to interior chambers (such as 30) of the containers. A number of outflow lines (such as 100) direct mixtures of inert gas and outgassed compounds from the containers (such as 20) to traps (such as 108) outside of the oven. The flow controller (such as 114) includes a number of valves (such as 122 and 124) to permit adjustment of the flow rate of the inert gas to each inflow line (such as 86).

A further preferred embodiment of the present invention relates to apparatus for collecting outgassed compounds from a sample comprising a source of an inert gas (such as 116) and means for directing the inert gas past the sample to collect substantially all of the outgassed compounds from the sample without contributing any extraneous outgassed compounds during the collection process.

A further preferred embodiment of the present invention includes a method of collecting outgassed compounds from a sample over the course of a predetermined test period. The method includes placing the sample within a container formed from an inert material (such as in 142) and then placing the container within an oven (such as in 144) to maintain the container at a predetermined temperature. An inert gas is supplied to the container (such as in 146) to mix with the chemicals and compounds outgassed from the sample. The mixture of inert gas and outgassed compounds is then directed to a trap outside of the oven (such as in 148), and substantially all of the outgassed compounds are separated from the inert gas and retained within the trap (such as in 150).

The above specification and examples of preferred embodiments provide a complete description of the manufacture and use of the composition of the invention. Since many embodiments of the invention can be made without departing from the spirit and scope of the invention, the invention resides in the claims hereinafter appended.

It will be clear that the present invention is well adapted to attain the ends and advantages mentioned as well as those inherent therein. While a presently preferred embodiment has been described for purposes of this disclosure, numerous changes may be made which will readily suggest themselves to those skilled in the art and which are encompassed in the spirit of the invention disclosed and as defined in the appended claims.

What is claimed is:

1. Apparatus for collecting outgassed compounds from a sample, the apparatus comprising:
    a container defining an interior chamber to receive the sample, the interior chamber bounded by a bottom surface, an interior wall and a top surface, where each of the bottom surface, the interior wall and the top surface are formed from an inert material to surround the sample with the inert material, the inert material selected from the group consisting of Teflon, Delrin and polypropylene;
    an oven for maintaining the container at a predetermined temperature;
    a source of an inert gas;
    a flow controller connected to the source of inert gas to provide a predetermined flow rate of the inert gas;
    an inflow line connected between the flow controller and the interior chamber of the container to mix the inert gas with the outgassed compounds within the interior chamber;
    an outflow line formed from an inert material, the outflow line having a first end connected to the interior chamber of the container and having a second end extending outside of the oven; and
    a trap connected to the second end of the outflow line to receive a mixture of the inert gas and the outgassed compounds from the outflow line and separate substantially all of the outgassed compounds from the inert gas.

2. An apparatus as defined in claim 1 wherein:
    a substantial portion of the container is formed from the same inert material used to form the interior chamber.

3. An apparatus as defined in claim 1, wherein the outflow line is formed from one of Teflon, Delrin and polypropylene.

4. An apparatus as defined in claim 1, wherein the inflow line is formed from stainless steel.

5. An apparatus as defined in claim 1, further comprising a flow meter connected to the trap to measure a flow rate of inert gas exhausted from the trap.

6. An apparatus as defined in claim 1, further comprising:
    a plurality of containers positioned within the oven;
    a plurality of inflow lines connected between the flow controller and the plurality of containers;
    a plurality of traps; and
    a plurality of outflow lines connected between the containers and the traps; and wherein the flow controller further comprises:

a plurality of valves connected to the inflow lines, each valve permitting adjustment of the predetermined flow rate to one of the plurality of inflow lines.

7. An apparatus as defined in claim 6 wherein six inflow lines are connected between the flow controller and six containers within the oven, the flow controller further comprising:

two mass flow valves connected to the source of inert gas; and three feeder valves connected to each of the mass flow valves, each feeder valve connected to one of the inflow lines to regulate the predetermined flow rate of inert gas to one of the containers within the oven.

8. A method of collecting outgassed compounds from a sample comprising steps of:

(a) placing the sample within a container formed substantially entirely from an inert material to surround the sample with the inert material, the inert material selected from the group consisting of Teflon, Delrin and polypropylene;

(b) placing the container within an oven to maintain the container at a predetermined temperature;

(c) supplying an inert gas at a predetermined flow rate to the container to mix the inert gas with the outgassed compounds;

(d) directing the mixture of inert gas and outgassed compounds to a trap positioned outside of the oven; and (e) separating substantially all of the outgassed compounds from the inert gas and retaining the outgassed compounds within the trap.

9. A method as defined in claim 8, wherein step (d) further comprises connecting an outflow tubing made from an inert material between the container and the trap.

10. A method as defined in claim 8, wherein steps (c), (d) and (e) occur continuously over a period of time ranging between one and three hours.

11. A method of collecting outgassed compounds from a sample comprising steps of:

(a) placing the sample within an interior chamber of a container, the interior chamber bounded by a bottom surface, an interior wall and a top surface, where each of the bottom surface, the interior wall and the top surface are formed from an inert material to surround the sample with the inert material, the inert material selected from the group consisting of Teflon, Delrin and polypropylene;

(b) supplying an inert gas at a predetermined flow rate to the interior chamber to mix the inert gas with the outgassed compounds; and (c) separating substantially all of the outgassed compounds from the inert gas.

12. A method as defined in claim 11, wherein the placing step (a) further comprises hermetically sealing the sample within the interior chamber of the container.

13. A method as defined in claim 11, further including the step of:

(d) maintaining the container at a predetermined elevated temperature.

14. A method as defined in claim 13, wherein:

the maintaining step (d) further comprises placing the container within an oven; and the separating step (c) further comprises directing the mixture of inert gas and outgassed compounds to a trap positioned outside of the oven to separate the outgassed compounds from the inert gas.

15. A method as defined in claim 14, wherein the separating step (c) further comprises connecting an outflow tubing formed from an inert material between the interior chamber and the trap.

16. A method as defined in claim 15 wherein the outflow tubing is formed from one of Teflon, Delrin and polypropylene.

17. A method as defined in claim 11, wherein the separating step (c) further comprises directing the mixture of inert gas and outgassed compounds to a trap to separate the outgassed compounds from the inert gas.

18. A method as defined in claim 17, wherein the separating step (c) further comprises connecting an outflow tubing formed from an inert material between the interior chamber and the trap.

\* \* \* \* \*